United States Patent [19]

Langelier et al.

[11] Patent Number: 5,002,932

[45] Date of Patent: Mar. 26, 1991

[54] ANTIVIRAL PHARMACEUTICAL COMPOSITIONS AND METHOD OF TREATING HERPES

[76] Inventors: Yves Langelier, 4671 Christophe Colomb, Montreal, Quebec, Canada, H2J 3G7; Pierrette Gaudreau, 776 Adrien, Greenfield Park, Quebec, Canada, J4V 3L4; Paul Brazeau, 12460 Odette Oligny, Cartierville (Montreal), Quebec, Canada, H4J 9Z7

[21] Appl. No.: 275,891

[22] Filed: Nov. 25, 1988

[30] Foreign Application Priority Data

Nov. 24, 1987 [CA] Canada .................................. 552632

[51] Int. Cl.$^5$ .......................... A61K 37/02; C07K 7/64
[52] U.S. Cl. ............................................. 514/9; 514/8; 514/10; 514/11; 530/320
[58] Field of Search .......................... 514/8, 9, 10, 11; 530/320

[56] References Cited

U.S. PATENT DOCUMENTS

| | | | |
|---|---|---|---|
| 3,251,738 | 5/1966 | Scherr | 514/11 |
| 3,751,562 | 8/1973 | Nichols | 514/11 |
| 4,188,373 | 2/1980 | Krezanoski | 424/78 |
| 4,199,574 | 4/1980 | Schaeffer | 424/200 |
| 4,294,831 | 10/1981 | Schaeffer | 424/253 |
| 4,323,573 | 4/1982 | Schaeffer | 424/253 |
| 4,360,522 | 11/1982 | Schaeffer | 424/253 |
| 4,568,665 | 2/1986 | Mitchell | 514/11 |
| 4,795,740 | 1/1989 | Cohen et al. | 514/14 |

FOREIGN PATENT DOCUMENTS

| | | | |
|---|---|---|---|
| 792544 | 3/1958 | United Kingdom | 514/9 |
| 2167296 | 5/1986 | United Kingdom . | |

OTHER PUBLICATIONS

Physician's Desk Reference, 41st ed., Medical Economics, Inc., Oradell, N.J., U.S.A., 1987, pp. 814–818.
B. Alarcon et al., Antiviral Research, 4, 231 (1984).
T. A. Krenitsky et al., Proc. Natl. Acad. Sci. U.S.A. 81, 3209 (1984).
G. A. Brewer in "Analytical Profiles of Drug Substances", vol. 9, Academic Press, New York, N.Y., U.S.A., 1980, pp. 1–69.

*Primary Examiner*—Lester L. Lee
*Assistant Examiner*—A. Davenport
*Attorney, Agent, or Firm*—David E. Frankhouser; Daniel Reitenbach; Mary-Ellen M. Timbers

[57] ABSTRACT

Disclosed herein is a combination of bacitracin and acyclovir or equivalent derivatives thereof. The combination, as well as bacitracin itself, are useful for treating herpes viral infections.

15 Claims, No Drawings

ANTIVIRAL PHARMACEUTICAL COMPOSITIONS AND METHOD OF TREATING HERPES

FIELD OF THE INVENTION

This invention relates to an antiviral pharmaceutical composition of a combination of acyclovir, or a related derivative thereof, and bacitracin. This invention also relates to a method of treating herpes infections in a mammal by administering bacitracin or the combination to the mammal.

BACKGROUND OF THE INVENTION

Acyclovir has become an antiviral agent of choice for the treatment of genital herpes simplex infections. Two related compounds, 6-deoxyacyclovir and the 6-deoxy-6-amino analog are being developed as agents for treating herpes infections. However, these agents are not without side effects. For example, skin rashes and renal impairment have been reported as side effects for acyclovir (see Physicians' Desk Reference, 41st ed., Medical Economics Inc., Oradell, N.J., USA, 1987, pp 814–818). Hence, safety as well as cost advantages should be realized if these agents could be formulated in a manner so that their activity is enhanced.

Unexpectedly, we have found that the antiviral activity of acyclovir, or a functionally equivalent derivative thereof, can be significantly enhanced by combining the same with the antibiotic bacitracin. This finding is even more surprising when viewed in the light of some of the published reports on bacitracin. Namely, A. Alarcon et al., Antiviral Research, 4, 231 (1984) have reported that bacitracin, when used alone, is inactive against herpes simplex virus type 1 (HSV-1); notwithstanding an earlier disclosure by J. Z. Krezanoski in U.S. Pat. No. 4,188,373, issued Feb. 12, 1980, incidentally listing bacitracin in a long list of antimicrobials for treating fungal and viral diseases without distinguishing which antimicrobial is used for which purpose. Also, R. Segal et al., U.K. patent application 2167296, published May 29, 1986 have proposed a rather complex mixture of bacitracin, neomycin and glycyrrhizin for treating oral infections. Thus, the enhancement of the antiviral activity found with the straight forward combination of this invention represents an unexpected turn of events. As a result, however, a relatively safe and economical pharmaceutical formulation and method for treating herpes infections are realized.

SUMMARY OF THE INVENTION

Provided herein is a pharmaceutical composition for treating herpes infections in a mammal comprising a pharmaceutically or veterinarily acceptable carrier, and an anti-herpes virally effective amount of a combination of bacitracin or a therapeutically acceptable salt thereof, and a compound of formula 1

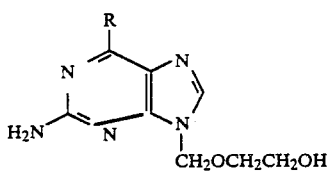

wherein R is hydroxy, hydrogen or amino, or a therapeutically acceptable salt thereof.

A preferred pharmaceutical composition of this invention for treating herpes infections comprises a pharmaceutically or veterinarily acceptable carrier and an anti-herpes virally effective amount of a combination of bacitracin or a therapeutically acceptable salt thereof, and the compound of formula 1 in which R is hydroxy or a therapeutically acceptable salt thereof.

Also provided herein is a method of treating herpes viral infections in a mammal. The method comprises administering to the mammal an anti-herpes virally effective amount of a combination of a compound of formula 1 or a therapeutically acceptable salt thereof and bacitracin or a therapeutically acceptable salt thereof.

DETAILS OF THE INVENTION

The compounds of formula 1 and their therapeutically acceptable salts are well known. For example, they are described by H. J. Schaeffer in U.S. Pat. No. 4,199,574, issued Apr. 22, 1980; see also H. J. Schaeffer et al., Nature (London), 272, 583 (1978) and T. A. Krenitsk et al., Proc. Natl. Acad. Sci. USA, 81, 3209 (1984). The compound of formula 1 wherein R is hydroxy has the nonproprietary name, acyclovir, and the chemical name, 9-((2-hydroxyethoxy)methyl)guanine. The compound of formula 1 wherein R is hydrogen has the names 6-deoxyacyclovir and 2-amino-9-((2-hydroxyethoxy)methyl)adenine, and the compound of formula 1 wherein R is amino has the chemical name, 2,6-diamino-9-(2-hydroxyethoxy)methyl)purine.

It is to be understood that the compound of formula 1 in which X is hydroxy can exist in its tautomeric form, i.e. 2-amino-1,9-dihydro-9-((2-(hydroxyethoxy)methyl)-6H-purin-6-one, and that the compound can be a mixture of the two tautomeric forms, the percentage of each tautomer in the mixture being dependent on the physical environment of the compound.

Although the preceding embodiments of this invention are based on a combination of bacitracin and a compound of formula 1, including acyclovir, a combination of bacitracin and any functionally equivalent derivation of acyclovir also is included within the scope of this invention. For example, such derivatives of acyclovir are disclosed by H. J. Schaeffer in U.S. Pat. No. 4,199,574, supra; U.S. Pat. No. 4,294,831, issued Oct. 13, 1981; U.S. Pat. No. 4,323,573, issued Apr. 6, 1982 and U.S. Pat. No. 4,360,522, issued Nov. 23, 1982.

Bacitracin and its therapeutically acceptable salts, for instance, zinc bacitracin, manganese bacitracin, sodium bacitracin and bacitracin methylenedisalicyclic acid, are described by G. A. Brewer in 'Analytical Profiles of Drug Substances', volume 9, Academic Press, New York, N.Y., USA, 1980, pp 1–69.

The term "pharmaceutically acceptable carrier" or "veterinarily acceptable carrier" as used herein means a non-toxic, generally inert vehicle for the active ingredient which does not adversely affect the ingredient.

The term "physiologically acceptable carrier" as used herein means an acceptable cosmetic vehicle of one or more non-toxic excipients, which do not react with the active ingredients contained therein or reduce their effectiveness.

The term "effective amount" as used herein means a predetermined antiviral amount of the combination of this invention sufficient to be effective against the viral organisms in vivo.

The antiviral activity of the combination of this invention can be demonstrated by biochemical, microbiological and biological procedures showing the inhibitory effect of the combination on the replication of HSV-1 and HSV-2, and other herpes viruses, for example, varicella zoster virus (VZV), Epstein-Barr virus (EBV), equine herpes virus (EHV) and pseudorabies virus (PRV).

For example, a method for demonstrating the inhibitory effect of the combination on viral replication is the cell culture technique; see, for example, T. Spector et al., Proc. Natl. Acad. Sci. USA, 82, 4254 (1985). This method in a modified form is exemplified hereinafter.

A method for demonstrating the therapeutic effect of the combination is the guinea pig model for cutaneous herpes simplex viral infections; see, for example, S. Alenius and B. Oberg, Archives of Virology, 58, 277 (1978).

When utilizing the combination of this invention for treating viral infections, the combination is administered to warm blooded animals, e.g. humans, pigs or horses, in a vehicle comprising one or more pharmaceutically acceptable carriers, the proportion of which is determined by the solubility and chemical nature of acyclovir or related derivatives and bacitracin, chosen route of administration and standard biological practice. Preferably, the combination is administered topically. For example, the two active agents (i.e. the compound of formula 1 and bacitracin, or their therapeutically acceptable salts) can be formulated in the form of solutions, emulsions, creams, or lotions in pharmaceutically acceptable vehicles. Such formulation can contain 0.1–5.0 percent, preferably 0.1 to 1.0 percent, by weight, of the compound of formula 1, or a therapeutically acceptable salt thereof, and about 0.025 to 5.0%, preferably 0.05 to 1.0%, by weight, of bacitracin, or a therapeutically acceptable salt thereof.

One preferred embodiment of this invention involves an antiviral pharmaceutical composition for treating herpes viral infections of the skin or part of the oral or genital cavity. This composition comprises a combination of 0.1 to 5.0 percent by weight of the compound of formula 1 in which R is hydroxy, 0.025 to 5.0 percent by weight of bacitracin or zinc bacitracin (specific activity ranging from 40 to 65 units per mg), together with a pharmaceutically acceptable carrier. Preferred carriers in this instance are water soluble ointment bases or water-oil type emulsions.

Examples of suitable excipients or carriers for the above mentioned formulations are found in standard pharmaceutical texts, e.g. in "Remington's Pharmaceutical Sciences", 16th ed, Mack Publishing Company, Easton, Pa., 1980.

The dosage of the combination of this invention will vary with the form of administration and the particular active agents for the combination chosen. Furthermore, it will vary with the particular host under treatment. Generally, treatment is initiated with small dosages substantially less than the optimum dose of the combination. Thereafter, the dosage is increased by small increments until the optimum effect under the circumstances is reached. In general, the combination is most desirably administered at a concentration level that will generally afford antiviral effective results against herpes virus without causing any harmful or deleterious side effects.

The combination is administered topically to the infected area of the body, eg. the skin or part of the oral or genital cavity, in an amount sufficient to cover the infected area. The treatment should be repeated, for example, every four to six hours until lesions heal, usually within three to eight days. No contraindications have been observed.

Although the method of treating herpes viral infections can be most advantageously practiced by administering the combination of the compound of formula 1 and bacitracin simultaneously in a formulation, the separate or sequential administration on a daily basis of the two active agents is also encompassed within the scope of this invention.

Another embodiment of this invention comprises a cosmetic composition comprising a herpes viral prophylactic amount of the combination of this invention, together with a physiologically acceptable cosmetic carrier. Additional components, for example, skin softeners, may be included in the formulations. The cosmetic formulation of this invention is used prophylactically to prevent the outbreak of herpetic lesions. They can be applied nightly and generally contain less of the two active agents of the combination than pharmaceutical preparations. A preferred range for the amount of each of the agents in the cosmetic composition is 0.025 to 0.2 percent by weight.

The following example further illustrates this invention. Bacitracin was obtained from Sigma Chemical Corporation, St. Louis, Mo., USA and the acyclovir from Bourroughs Wellcome, Inc., Kirkland, P.Q., Canada.

Comparison of Acyclovir. Bacitracin and the Combination of the Two Agents in Inhibiting HSV-2 Replication Using Cell Culture Techniques.

(a) Preparation of serum-starved cells: A medium composed of alpha medium (Gibco Canada Inc, Burlington, Ontario, Canada) and fetal calf serum (Gibco Canada Inc.), in a 9:1 volume ratio, was placed in tissue culture dishes (35 mm, A/S Nunc, Kamstrup, Denmark). The medium in each dish was seeded with BHK 21/C13 cells (1.5 × 10$^6$ for each dish). (BHK 21/C13 cells have been described by Y. Langelier and G. Buttin, J. Gen. Virol., 57, 21 (1981)). After 6 hours, the medium was replaced with a new medium composed of alpha medium and fetal calf serum (99.5:0.5 v/v). The resultant preparation was incubated at 37° C. for 4 days.

(b) Cell infection in BBMT medium* without serum: The incubation medium was removed from the cells. The cells were washed twice with alpha medium (without the serum) and once with the BBMT medium. The cells were then incubated at 37° C. in BBMT medium for two hours. A series of viral solutions were prepared from a stock of HSV-2 (strain HG-52, described by Langelier and Buttin, supra) and the appropriate choice and amounts of the agents to be tested, diluted with BBMT to give viral solutions having a multiplicity of infection of 0.02 plaque forming units (PFU) per cell. A control viral solution (without any agent) also was prepared. Each viral solution (250 µl) was added to duplicate dishes containing the previously prepared cells in BBMT medium. After one hour of incubation at 37° C. for virus absorption, the medium in each dish was removed by aspiration. The cells were washed twice with BBMT medium. Fresh BBMT medium (800 µl), with or without (control) the appropriate concentration of the test agent, was added to the dishes which were further incubated at 37° C. Every six hours, a concentrated solution of bacitracin in BBMT was added to the appropriate dishes to maintain the initial concentration of that agent.

*BBMT medium is described by P. Brazeau et al., Proc. Natl. Acad. Sci. USA, 79, 7909 (1982).

(c) Harvesting: At 30 hours post-infection, cells were detached with a rubber policeman and frozen at −80° C. until titration.

(d) Titration: Virus titration were performed according to the method of B. B. Wentworth and L. French, Proc. Soc. Exp. Biol. Med., 131, 588 (1969).

The following table is illustrative of the results obtained when acyclovir, bacitracin and combinations thereof were tested for activity according to the preceding method. Results are expressed in PFU per cell for infected cells harvested at 30 hours post infection. The lower the PFU per cell value, the greater the inhibitory effect on viral replication of the tested agent.

| AGENT | PFU PER CELL | PFU per cell for control/ PFU per cell for agent |
|---|---|---|
| Control | 67.00 | 1.0 |
| Bacitracin | | |
| 0.25 mM | 1.08 | 62.0 |
| 0.50 mM | 0.13 | 515.0 |
| 0.75 mM | 0.014 | 4786.0 |
| 1.00 mM | 0.008 | 8375.0 |
| Acyclovir | | |
| 0.50 μM | 16.9 | 3.96 |
| 2.00 μM | 4.9 | 13.67 |
| Bacitracin + Acyclovir | | |
| 0.5 mM + 0.5 μM | 0.046 | 1456.5 |
| 0.5 mM + 2.0 μM | 0.018 | 3722.2 |
| 1.0 mM + 0.5 μM | 0.0012 | 55833.0 |
| 1.0 mM + 2.0 μM | 0.000038 | 1,763,158.0 |

The results expressed in the above table demonstrate the anti-herpes viral effect of acyclovir, bacitracin and the combination of the two agents. The results show that the combination of acyclovir and bacitracin in suitable proportions decreases viral production to a much greater degree than either of the agents alone. The greater effectiveness of the combination is strikingly illustrated by the ratio, $$\frac{PFU \text{ per cell for control}}{PFU \text{ per cell for agent}},$$

expressing the relative effectiveness of acyclovir, bacitracin and the combination thereof.

The preceding results also demonstrate the surprising finding, in view of the general knowledge of the microbiological properties of bacitracin and the prejudicial report of Alacorn et al., supra, that bacitracin exhibits an antiviral effect against herpes virus. Hence, the scope of the present invention includes a method of treating herpes viral infections in a mammal which comprises administering to the mammal an anti-herpes virally effective amount of bacitracin or a therapeutically acceptable salt thereof. When bacitracin or a therapeutically acceptable salt is used for this purpose, the agent is administered topically in pharmaceutical compositions in the manner described herein for the combination. Such topical compositions can contain from 0.025 to 5.0 percent, preferably 0.1 to 2.0 percent, by weight of the composition, of bacitracin or a therapeutically acceptable salt thereof. Topical cosmetic formulations of bacitracin or a therapeutically acceptable salt thereof, can contain 0.05 to 0.5 percent by weight of the composition of the active agent, and can be formulated and used in the same manner described above for a cosmetic composition of the combination.

The embodiments of this invention in which an exclusive property or privilege is claimed are defined as follows:

1. A pharmaceutical composition for treating herpes infections in a mammal consisting essentially of a pharmaceutically or veterinarily acceptable carrier, and an effective amount of the following combination:

(a) an effective amount of a compound of formula 1

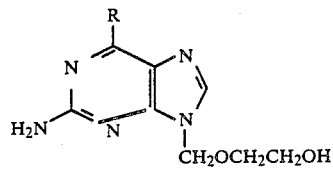

wherein R is hydroxy, hydrogen, or amino, or a therapeutically acceptable salt thereof; and (b) bacitracin or a therapeutically acceptable salt thereof, in an amount sufficient to enhance the anti-herpes viral activity of the compound of formula 1 or the therapeutically acceptable salt thereof.

2. A pharmaceutical composition of claim 1 wherein R of the compound of formula 1 is hydroxy.

3. A pharmaceutical composition of claim 1 wherein R of the compound of formula 1 is hydrogen.

4. A pharmaceutical composition of claim 1 wherein R of the compound of formula 1 is amino.

5. A pharmaceutical composition of claim 1 wherein the amount of the compound of formula 1, or a therapeutically acceptable salt thereof, is 0.1 to 5.0 percent by weight of the composition, and the amount of bacitracin, or a therapeutically acceptable salt thereof, is 0.025 to 5.0 percent by weight of the composition.

6. A pharmaceutical composition of claim 5 comprising 0.1 to 5.0 percent by weight of the compound of formula 1 wherein R is hydroxy, and 0.025 to 5.0 percent by weight of bacitracin or zinc bacitracin.

7. A cosmetic composition consisting essentially of a herpes viral prophylactic amount of the following combination:

(a) an anti-herpes viral compound of formula 1

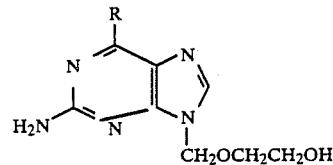

wherein R is hydroxy, hydrogen or amino, or a therapeutically acceptable salt thereof;

(b) bacitracin or a therapeutically acceptable salt thereof, in an amount sufficient to enhance the anti-herpes viral activity of the compound of formula 1 or the therapeutically effective salt thereof; and (c) a physiologically acceptable carrier.

8. A method of treating herpes viral infections in a mammal comprising administering thereto an effective amount of the pharmaceutical composition of claim 1.

9. A method of claim 8 wherein the combination comprises bacitracin or zinc bacitracin and the compound of formula 1 wherein R is hydroxy.

10. A method of claim 8 wherein the viral infection is one selected from the group of herpes simplex type 1, herpes simplex type 2, varicella zoster, Epstein-Barr, equine herpes and pseudorabies viral infections.

11. A method of claim 8 wherein the combination is administered topically.

12. A method of treating herpes viral infections in a mammal which comprises administering thereto a combination, consisting essentially of:

(a) an effective amount of a compound of formula 1

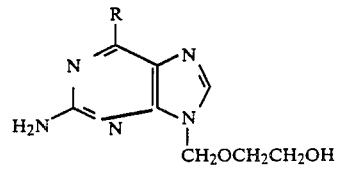

wherein R is hydroxy, hydrogen, or amino, or a therapeutically acceptable salt thereof; and
(b) bacitracin or a therapeutically acceptable salt thereof, in an amount sufficient to enhance the anti-herpes viral activity of the compound of formula 1 or the therapeutically acceptable salt thereof.

13. A method of claim 12 wherein the combination comprises bacitracin or zinc bacitracin and the compound of formula 1 wherein R is hydroxy.

14. A method of claim 12 wherein the bacitracin and the compound of formula 1 are administered sequentially or simultaneously.

15. A method of claim 12 wherein the viral infection is one selected from the group of herpes simplex type 1, herpes simplex type 2, varicella zoster, Epstein-Barr, equine herpes and pseudorabies viral infections.

* * * * *